United States Patent [19]

Nishino

[11] 4,221,777
[45] Sep. 9, 1980

[54] METHOD FOR PREPARING A PANCREATIC GLUCAGON SPECIFIC ANTIBODY

[75] Inventor: Tomoyoshi Nishino, Tokushima, Japan

[73] Assignee: Otsuka Pharmaceutical Co., Ltd., Tokyo, Japan

[21] Appl. No.: 924,319

[22] Filed: Jul. 13, 1978

Related U.S. Application Data

[62] Division of Ser. No. 876,799, Feb. 10, 1978.

[30] Foreign Application Priority Data

Feb. 10, 1977 [JP] Japan .................................. 52-13919

[51] Int. Cl.$^2$ ...................... C07G 7/00; C07C 103/52; G01N 23/00; G01N 33/00
[52] U.S. Cl. ................................ 424/12; 23/230 B; 260/112 R; 260/112 B; 260/112.5 R; 260/121; 424/1; 424/85; 424/177; 424/180
[58] Field of Search .................. 424/1, 2, 8, 12, 13, 424/85, 177, 180; 260/112.5 R, 112 R, 112 B, 121; 23/230 B

[56] References Cited

U.S. PATENT DOCUMENTS

| | | | |
|---|---|---|---|
| 3,553,310 | 1/1971 | Csizmas | 424/12 X |
| 3,794,630 | 2/1974 | Mullan et al. | 424/177 |
| 3,975,342 | 8/1976 | Gross | 424/12 X |
| 3,996,345 | 12/1976 | Ullman | 424/12 |
| 4,075,194 | 2/1978 | Sela et al. | 260/112.5 R |

FOREIGN PATENT DOCUMENTS

1257263 12/1971 United Kingdom ...................... 424/12

OTHER PUBLICATIONS

Avrameas et al., Immunochem., vol. 6, 1969, pp. 53-66.

*Primary Examiner*—Anna P. Fagelson
*Attorney, Agent, or Firm*—Sughrue, Rothwell, Mion, Zinn and Macpeak

[57] ABSTRACT

A method for preparing an antigen comprising a peptide-protein complex which comprises reacting a peptide represented by the general formula (I)

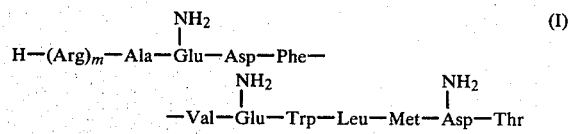

wherein m is 0 or 1, as a hapten, with a protein as a carrier in the presence of a dialdehyde represented by the general formula (II)

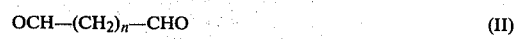

wherein n is an integer of 1 to 5 and a method for preparing an antibody specific to pancreatic glucagon comprising administering the above described antigen to a mammal and recovering the antibody produced.

7 Claims, 9 Drawing Figures

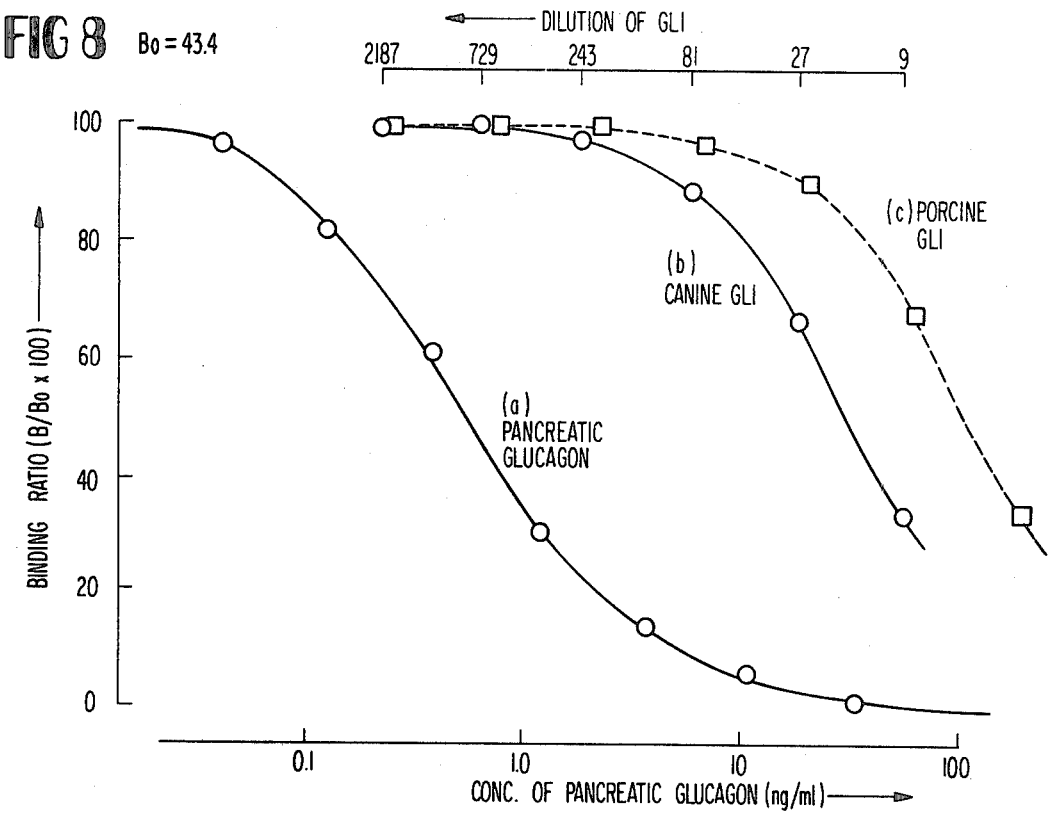
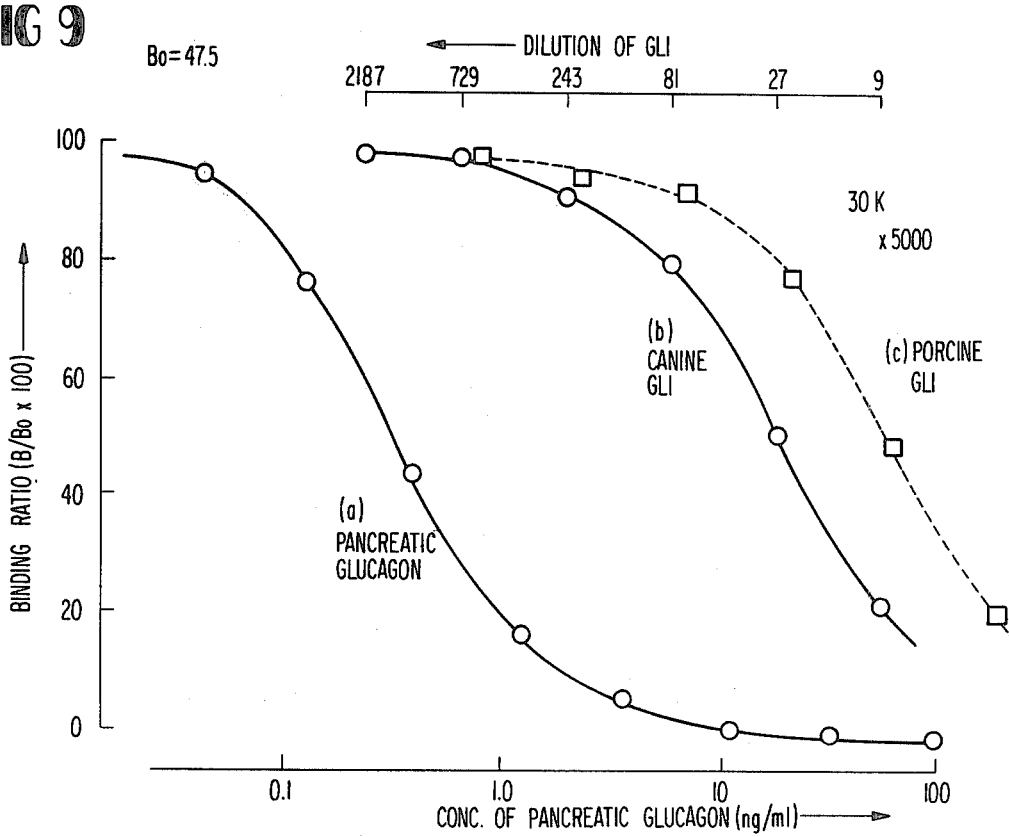

METHOD FOR PREPARING A PANCREATIC GLUCAGON SPECIFIC ANTIBODY

This is a division of application Ser. No. 876,799, filed Feb. 10, 1978.

BACKGROUND OF THE INVENTION

1. Field of the Invention

This invention relates to a method for preparing antigens comprising a peptide-protein complex and to a method for preparing antibodies using the antigens.

2. Description of the Prior Art

An antigen is a substance which stimulates a living organism to produce a specific antibody and react therewith specifically. That is, an antigen is a substance which has an antigenicity capable of forming an antibody in vivo and an immunoreactivity capable of reacting with the antibody in vitro. Representative examples of antigens are foreign proteins, such as bacteria, viruses, various toxins, etc. On the other hand, an antibody is a substance produced in a living organism, e.g., mammals, etc., due to the stimulation of an antigen and is present mainly in blood sera, in particular, in the γ-globulin fraction in blood sera. Antibodies can react with antigens in vitro or in vivo.

Antigens have on the surface thereof one or more determinant groups which can react with antibodies and antibodies have on the surface thereof one or more reacting groups which can combine with the determinant group(s). These two substances have a complementary spatial structure to each other called by Ehrlich a "key and key hole relationship" to which the specificity between antigens and antibodies is ascribable.

Most of the naturally found antigens are considered to have on the surface thereof a mosaic of various determinant groups and specific antibodies are considered to be produced corresponding to the respective determinants.

The antigen-antibody reaction occurring between antigens having common determinant groups and the corresponding antibodies is termed a "cross-reaction" or "group reaction."

An antigen-antibody reaction comprises a first step in which the antigen combines with a corresponding antibody in a very short time (e.g., 20 seconds) even at low temperatures, e.g., 0° C. to form a conjugater, and a second step in which the conjugates thus obtained combine with each other to cause agglutination which can be observed visually.

One of the characteristics of an antigen-antibody reaction is high specificity and such reaction has widely been utilized in the diagnosis of various diseases.

The determination of hormones has conventionally been conducted using an immunoreaction, i.e., an antigen-antibody reaction, as is well known in the art.

Pancreatic glucagon is one of the physiological pancreatic hormones which plays an important role in the uptake and metabolism of sugars and has the following amino acid sequence

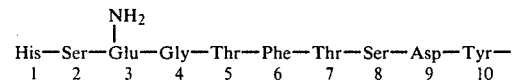

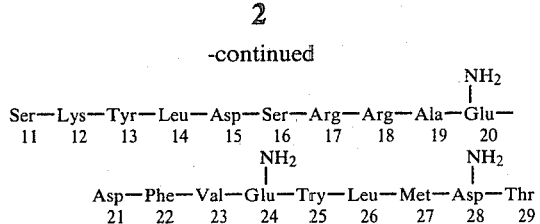

Quantitative determination of pancreatic glucagon has recently attracted much attention in the fields of diagnosis, pathology and the like since the determination of the level of pancreatic glucagon in blood makes it possible to diagnose various diseases or pathological states, for example, diabetes, etc.

The conventional method for determining pancreatic glucagon has been performed using a radioimmunoassay method (hereinafter referred to as RIA method) in which antibodies obtained using pancreatic glucagon per se or antigens which contain pancreatic glucagon as a hapten are employed. This RIA method is successful to some extent. [see Unger et al: *Proc. Soc. Exp. Biol. Med.* 102, 621 (1959)]

However, as research in the art proceeds the presence of glucagon-like substances which behave immunologically in a manner similar to pancreatic glucagon has been discovered in the digestive tract or gut of mammals and such is named "gut-GLI." [See Sutherland et al: *J. Biol. Chem.* 175, 663, (1964) and Unger et al.: *Metabolism*, 15, 865 (1966)] and it has also been discovered that the antibodies obtained using pancreatic glucagon per se or antigens which contain pancreatic glucagon as a hapten cross react not only with pancreatic glucagon but also with gut-GLI's so that they are non-specific to pancreatic glucagon. In other words in determining pancreatic glucagon using the RIA method, the above-described known antibodies give values which include values ascribable to the reaction with gut-GLI's resulting in a failure to provide a diagnostically exact determination.

It has recently been reported that pancreatic glucagon-specific antibodies were obtained by change using the same antigen as described above [see *Diabetes*, 17 (Suppl. 1), 321 (1968)].

However, it is also reported that these antibodies which are called "G 58" and "30 K" can be obtained only by chance and very rarely [see *Saishin Igaku (Newest Medicine)* 30 (11) p 1901 (1975) and Heading, L.G.: *Horm. Metab. Res.*, 1, 87–88 (1969)]. Therefore, the method for preparing antibodies using an antigen which contains pancreatic glucagon as a hapten has poor reproducibility and is not practically acceptable.

On the other hand, the structure-function relationship of glucagon has been investigated [see Assan et al.: *Diabetes*, 21, 843, (1972)] by synthesizing various peptides related to glucagon, i.e., $C_1$ to $C_{23}$ fragments, and determining their biological activity using the increase in blood sugar level as an indicator. Further, investigations were made on antigenic sites in the glucagon molecule using a glucagon-specific antibody "K 47" and a glucagon-non-specific antibody "PVP 8" leading to the assumption that there are at least two antigenic sites in the glucagon molecule and that one of these antigenic sites is present in the C-terminal portion, in particular the $C_{23}$–$C_{29}$ fragments, of the glucagon molecule.

Instead of progress in the investigation of the mechanism of the immunological behavior of glucagon or gut-GLI as above, however, no reports on the development of practically acceptable antibodies have been made.

As stated above, known antibodies are either non-specific to pancreatic glucagon or can be obtained with poor reproducibility so that development of techniques which can be used to produce antibodies with specificity to pancreatic glucagon on an industrial scale is strongly desired.

SUMMARY OF THE INVENTION

An object of this invention is to provide a method for preparing antibodies which are highly specific to pancreatic glucagon with high reproducibility.

Another object of this invention is to provide a method for preparing antigens suitable for preparing such pancreatic glucagon-specific antibodies.

Extensive investigations have been made in order to obtain a method for preparing antibodies which is useful for determining pancreatic glucagon using an RIA method and is sufficiently reproducible in determining antibodies highly specific to pancreatic glucagon on an industrial scale. During the investigation it has been found that the antigenicity to porcine pancreatic glucagon which has an amino acid sequence completely identical to that of human glucagon is present on the $C_{18}$ to $C_{29}$ or $C_{19}$ to $C_{29}$ amino acid sequence.

Based on this finding another extensive investigation was made to prepare antigens containing the above described peptides as a hapten and antibodies highly specific to pancreatic glucagon using such antigens to complete this invention.

Therefore, this invention in one embodiment provides a method for preparing an antigen comprising a peptide-protein complex which comprises reacting a peptide represented by the general formula (I)

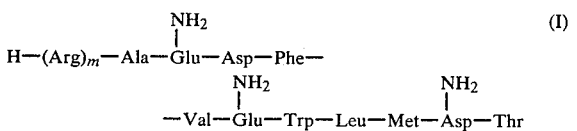

wherein m is 0 or 1, as a hapten, with a protein as a carrier in the presence of a dialdehyde represented by the general formula (II)

wherein n is an integer of 1 to 5.

This invention also in another embodiment provides a method for preparing a pancreatic glucagon specific antibody which comprises administering the antigen comprising a peptide-protein complex obtained above to a mammel to cause an antibody to be produced and recovering the resulting antibody.

BRIEF DESCRIPTION OF THE DRAWINGS

FIG. 8 is a graph showing the binding ratio (%) of Antibody (I) with standard glucagon, canine gut-GLI and porcine gut-GLI at each concentration and dilution; and FIG. 9 is a graph showing the binding ratio (%) of antibody 30 K with standard glucagon, canine gut-GLI and porcine gut-GLI at each concentration and dilution.

DETAILED DESCRIPTION OF THE INVENTION

Figure 1:
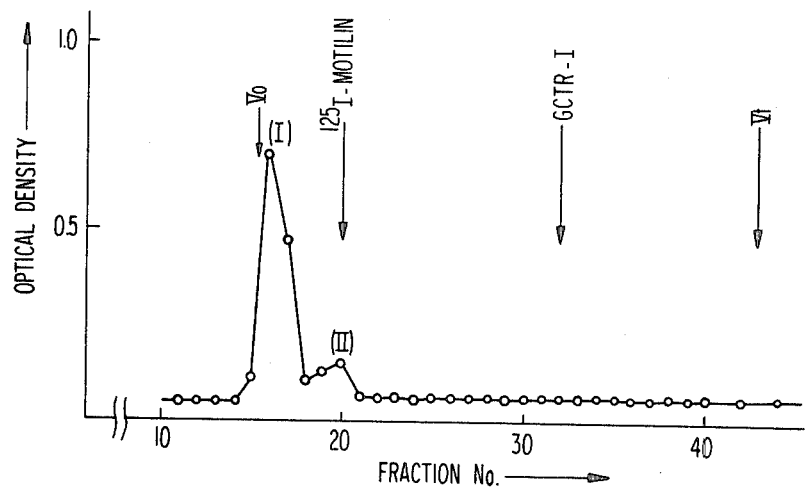
FIGS. 1 and 2 show, respectively, the molecular weight distribution and the UV absorption spectrum of the product obtained in Example 1 given hereinafter.

Standard abbreviations for amino acid residues employing amino acid nomenclature adopted by IUPAC are used herein to indicate the peptides used as a hapten in this invention.

The use of peptides represented by the formula (I) as a hapten is indispensable in this invention. For the peptides described above by the general formula (I), the peptide where m is 1 (hereafter referred to as "GCTR-1" for brevity) corresponds to the $C_{18}$–$C_{29}$ fragment of porcine pancreatic glucagon, and the peptide where m is 0 (hereafter referred to as "GCTR-2") corresponds to the $C_{19}$–$C_{29}$ fragment of porcine pancreatic glucagon. Both of these peptides are known compounds (W. W. Bromer, A. Staub, et al.: "The Amino Acid Sequence of Glucagon," *Journal of the American Chemical Society*, June 5, 1957).

In this invention GCTR-1 and GCTR-2 can be used individually or as a mixture thereof.

The dialdehydes represented by the general formula (II) serve as a link connecting the hapten and the protein.

Suitable examples of dialdehydes represented by the general formula (II) which can be used in this invention include malonaldehyde, succinaldehyde, glutaraldehyde, adipaldehyde, etc.

Any proteins conventionally used for preparing antigens can also be used as a carrier in this invention.

Representative examples of such proteins suitable as a carrier include equine serum albumin, bovine serum albumin, rabbit serum albumin, human serum albumin, equine serum globulin, bovine serum globulin, rabbit serum globulin, human serum globulin, etc.

The antigen according to this invention can be obtained by reacting the hapten represented by the formula (I) with a protein in the presence of a dialdehyde represented by the general formula (II) in the aqueous solution or an aqueous buffer solution of a pH of about 7 to about 10, preferably 8 to 9, at a temperature of about 0° to about 40° C., preferably near room temperature (20° to 25° C.), for about 1 to 24 hours.

Suitable examples of buffer solutions which can be used include a 0.2 N sodium hydroxide-0.2 M boric acid-0.2 M potassium chloride buffer solution, a 0.2 M sodium carbonate-0.2 M boric acid-0.2 M potassium chloride buffer solution, a 0.05 M sodium tetraborate-0.2 M boric acid-0.05 M sodium chloride buffer solution, a 0.1 M potassium dihydrogenphosphate-0.05 M sodium tetraborate buffer solution, etc.

The proportion of hapten, dialdehyde and carrier used in the method of this invention will vary depending on the conditions. However, a generally employed proportion by weight of carrier to hapten is about 2:1 to about 6:1, preferably 3:1 to 5:1 and a generally employed molar proportion of dialdehyde to hapten is about 5:1 to about 10:1.

After the completion of the reaction the antigens thus obtained can be isolated and purified with ease using conventional methods, e.g., dialysis, gel filtration, fractional precipitation, etc. The antigens of this invention can be stored, e.g., by lyophilization.

The antigens according to this invention contain on the average 5 to 15 moles of peptide per mole of protein used.

The antigen or antigens produced as described above can be used as a starting material for preparing antibodies highly specific to pancreatic glucagon. Antigens containing 9 to 12 moles of peptide per mole of protein are preferred since they are capable of providing antibodies having a higher grade.

In order to prepare antibodies, the antigens are administered to mammals using a conventional method [see Proc. Soc. Exp. Biol. Med. 128, 347, (1968)] and then the antibodies formed in the living organism are collected. This invention includes this method for preparing antibodies.

Mammals which can be used in this invention for preparing antibodies are not specifically limited and cattle and oxen, pigs, horses, rabbits, guinea pigs, etc. can be used with rabbits and guinea pigs being preferred because of ease of handling.

On preparing antibodies, a predetermined amount of antigen is diluted with physiological saline solution to a predetermined concentration, e.g., 0.5 to 2 mg/ml. This solution is then mixed with Complete Freund's adjuvant to prepare a dispersion, which is then administered to the mammal. For example, the above-described dispersion is administered to a rabbit intradermally in a dosage of about 0.5 to about 2 mg of antigen at a time. Thereafter, administration at a dosage of 0.5 to 2 mg can be repeated once every two weeks for 2 to 10 months, preferably 4 to 6 months.

Collection of antibodies can be performed by bleeding the immunized animal when a large amount of antibody is prepared after the last administration of the dispersion containing the antigen, generally 1 to 2 weeks after the last administration, and centrifuging the blood thus-obtained to separate antiserum (antibody).

According to the method of this invention, it is possible to constantly provide antibodies having excellent specificity to pancreatic glucagon based on the uniqueness of the antigen used.

The antibodies prepared according to this invention have excellent specificity to human pancreatic glucagon as described above and are useful for determining human pancreatic glucagon using an RIA method with high accuracy.

This invention will be described in more detail by the following Examples which are not to be construed as limiting the present invention. Unless otherwise indicated herein, all parts, percents, ratios and the like are by weight.

EXAMPLE 1

In 0.2 ml of a 0.2 N potassium hydroxide aqueous solution was dissolved 6 mg of GCTR-1 at room temperature. To the mixture were added 1 ml of a 0.2 N sodium hydroxide-0.2 M boric acid-0.2 M potassium chloride buffer solution of pH 9.0 (hereafter referred to simply as "buffer solution" for brevity) and 1 ml of the buffer solution having 20 mg of bovine serum albumin (hereinafter referred to as "BSA" for brevity) dissolved therein and 1 ml of a 0.05 M glutaraldehyde solution was added dropwise thereto. The reaction mixture which amounted to about 3 ml was allowed to react with stirring at room temperature for 24 hours.

Of the product thus obtained a 0.5 ml aliquot thereof was taken out and 0.5 ml of a 2% sodium dodecylsulfate (hereafter referred to as "SDS" for brevity) was added thereto. After heating this mixture to 100° C. to dissolve the precipitate formed followed by cooling, the mixture was subjected to gel filtration using Sephadex G-75 equilibrated with a 1% SDS solution to examine the molecular weight distribution of the product. The gel filtration was conducted under the following conditions:

Detection: Optical Density at 280 nm (OD$_{280}$)
Column Used: 1×40 cm
Eluting Velocity: 3 ml/hour
Eluting Solution: 1% SDS solution containing 0.5 M NaCl The results obtained are shown in FIG. 1.

In FIG. 1, the ordinate represents the optical density and the abscissa represents the fraction number. The amount of each fraction was 1 ml.

From the results shown in FIG. 1 it can be been that the reaction product showed two distinct peaks at fraction Nos. 14 to 17 [Fraction (I)] and fraction Nos. 18 to 21 [Fraction (II)]. Fraction (I) had a molecular weight of about 75,000 or more which is higher than the molecular weight of motilin (about 2,700) and Fraction (II) had a molecular weight similar to the molecular weight of motilin. Both Fraction (I) and Fraction (II) had a molecular weight much higher than the molecular weight of GCTR-1 (about 1,000).

Further, Fractions (I) and (II) were dissolved with heating in a 2% SDS solution at a concentration of 0.5 mg/ml, respectively. After cooling, each solution was charged into a cell of 1 cm in length and the UV absorption at a wavelength range of 240 to 300 nm was measured. The results obtained are shown in FIG. 2.

Figure 2:
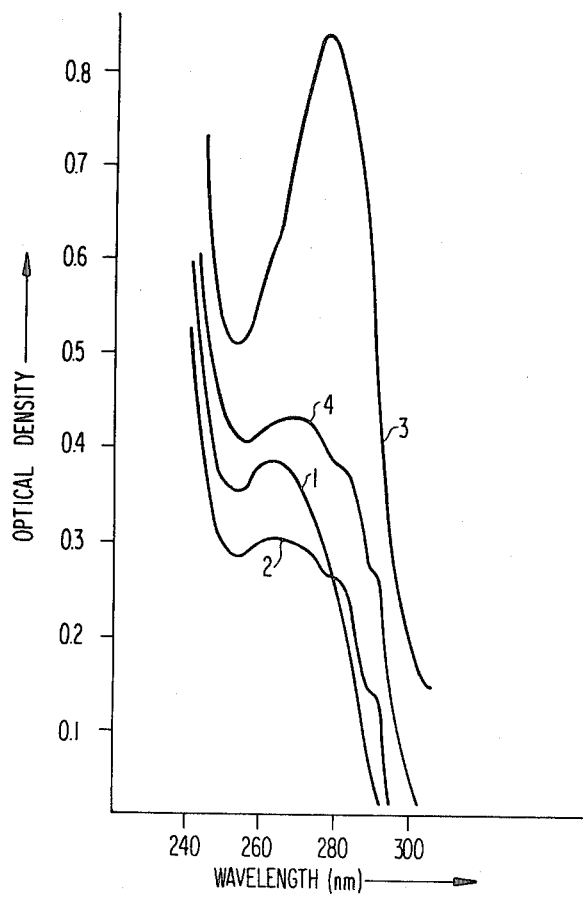

In FIG. 2, the ordinate represents the optical density and the abscissa represents the wavelength (nm). Numerals 1 and 2 denote the absorption patterns of Fractions (I) and (II), respetively. Numerals 3 and 4 denote the absorption patterns of BSA and GCTR-1, respectively, measured under the same conditions as in the case of Fractions (I) and (II).

From the results shown in FIG. 2, Fraction (I) (Curve 1) showed an absorption pattern different from the absorption patterns of BSA and GCTR-1. Taking into consideration the results shown in FIG. 1 on the molecular weight distribution, Fraction (I) was found to correspond to the peptide-protein (i.e., GCTR-1-BSA) complex. On the other hand, Fraction (II) (Curve 2) showed an absorption pattern of the same tendency as GCTR-1 (Curve 4). In view of the results shown in FIG. 1, Fraction (II) was found to correspond to a dimer of GCTR-1 formed by glutaraldehyde treatment thereof.

Another aliquot of the product (about 2.5 ml) was subjected to gel filtration in the same manner as described above and the fractions corresponding to Fraction (I) were collected and dialyzed with 0.6% sodium chloride solution at 4° C. for 24 hours followed by lyophilization to obtain white powders of GCTR-1-BSA complex in an amount of 17.3 mg. The complex thus obtained was a complex of 1 mole of BSA with on the average 11 moles of GCTR-1 coupled thereto. The binding ratio (%) was obtained as follows.

That is, at first a standard curve for the concentration of GCTR-1 vs. UV adsorption was prepared based on the fact that FIG. 1 did not show the presence of unreacted BSA, and the amount of Fraction (II) was calculated from this standard curve. Then, the amount of Fraction (II) was deduced from the amount of GCTR-1 initially charged. The resulting amount of GCTR-1 was assumed to correspond to the amount of GCTR-1 coupled to BSA.

EXAMPLE 2

The same procedures as described in Example 1 were repeated except that 6 mg of GCTR-2 was used in place of GCTR-1. The product thus-obtained was subjected to gel filtration under the same conditions as described in Example 1 and the molecular weight distribution and UV absorption were measured as in Example 1.

Figure 3:
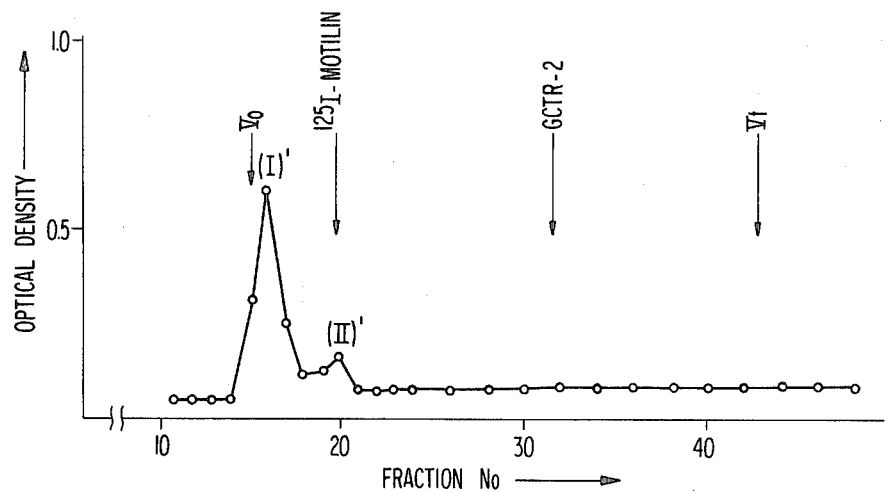
FIGS. 3 and 4 show, respectively, the molecular weight distribution and the UV absorption spectrum of the product obtained in Example 2 given hereinafter.
Figure 4:
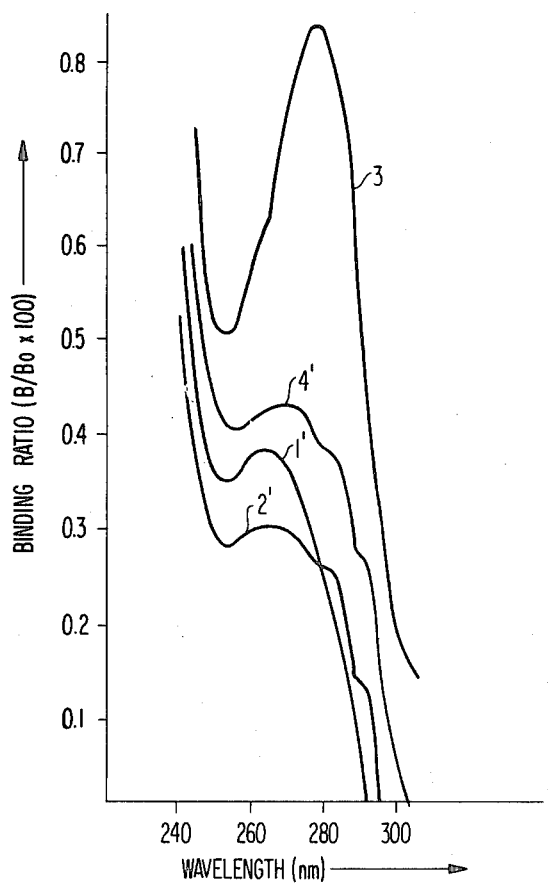

The results obtained are shown in FIGS. 3 and 4.

From the results shown in FIG. 3 it can be seen that the reaction product showed two distinct peaks [Fraction (I') and Fraction (II')] similar to the results of Example 1. Fractions (I') and (II') were found to correspond to GCTR-2-BSA complex and a dimer of GCTR-2, respectively, both having approximately the same molecular weight as Fraction (I) and Fraction (II'), respectively.

Fraction (I') was dialyzed and lyophilized in the same manner as in Example 1 to obtain white powders of GCTR-2-BSA complex in an amount of 17.8 mg. The complex thus obtained contained on the average 10 moles of GCTR-2 per mole of BSA.

EXAMPLE 3

7 mg of each of the antigens, i.e., the complexes prepared according to Examples 1 and 2, was dissolved in 1.8 ml of physiological saline solution and 2.7 ml of Complete Freund's Adjuvant was added thereto to form a dispersion. The dispersion thus-obtained was administered intradermally by injection to rabbits at a dose of 1 ml per rabbit. After 2 weeks another 1 ml of the dispersion was administered to each rabbit. Then a freshly prepared dispersion of 3 mg of antigen, 3 ml of physiological saline solution and 3 ml of Complete Freund's Adjuvant was administered intradermally at 2 week intervals for 3.5 months to immunize each test animal. Ten days after the last administration of the dispersion, each test animal was bled and the blood thus-obtained was centrifuged to separate antiserum, the antibody of this invention.

The activity of the antibody thus-obtained was measured as follows.

Antibody Activity Determination

Each of the antibodies, i.e., Antibody (I) prepared using the antigen obtained according to Example 1 and Antibody (II) prepared using the antigen obtained according to Example 2, was initially diluted with physiological saline solution to concentrations of $10^{-1}$, $10^{-2}$, $10^{-3}$, $10^{-4}$ and $10^{-5}$. To 100 µl of each diluted solution were added 100 µl of $^{125}$I-glucagon and 300 µl of a 0.5 M phosphate buffer of pH 7.5 (containing 0.5% by weight of BSA, 0.1% by weight of NaN$_3$ and 0.14 M NaCl) and the mixture was incubated at 4° C. for 48 hours and the resulting complex of $^{125}$I-glucagon and anti-serum was separated from unreacted or free $^{125}$I-glucagon using Dextran-coated charcoal and centrifugation at 4° C. at a speed of 3000 rpm for 15 minutes. Radioactivity of the complex thus obtained was counted to determine the binding ratio (%) of $^{125}$I-glucagon and antiserum at each concentration.

Figure 5:
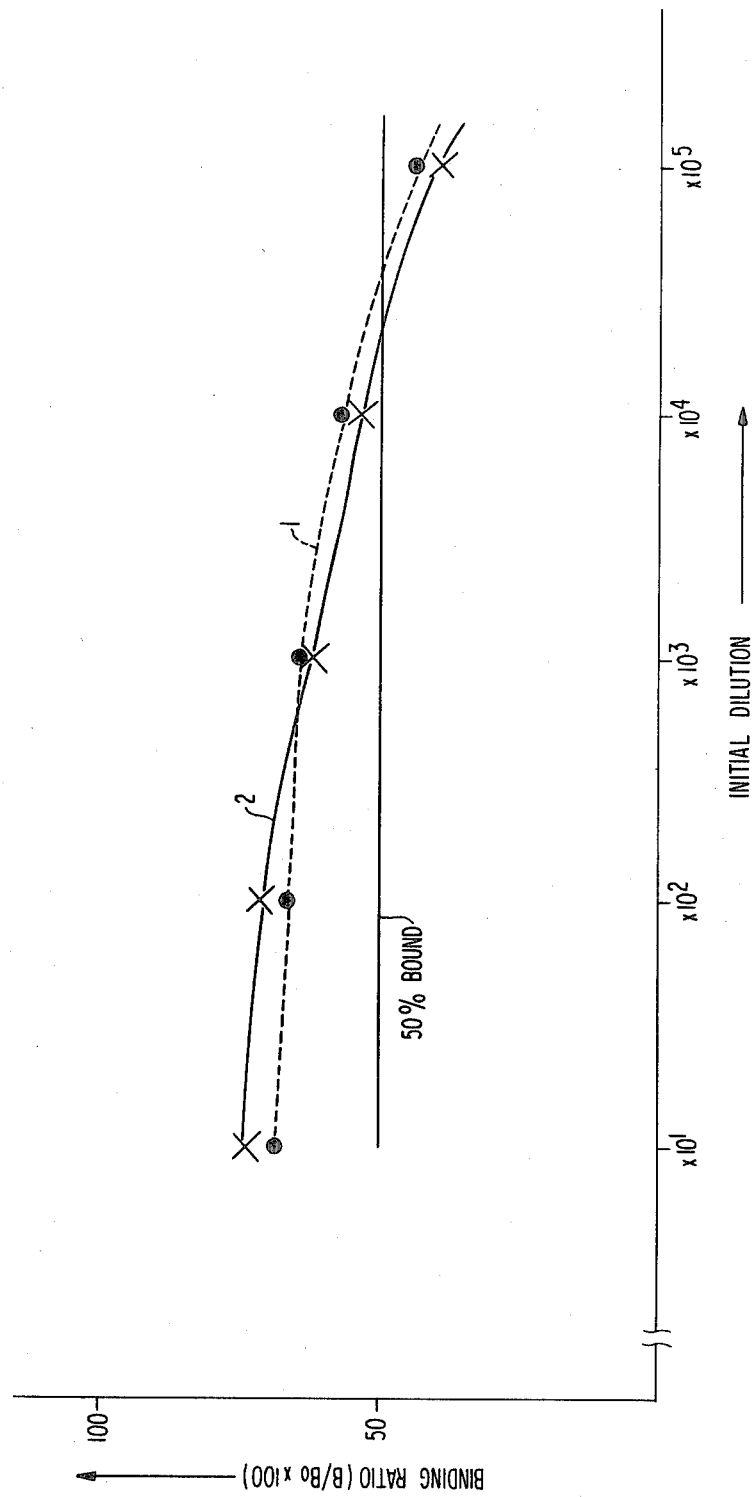
FIG. 5 shows a graph representing the immunoreactivity of the antibody obtained in Example 3 given hereinafter.

The results obtained are shown in FIG. 5. In FIG. 5, the ordinate represents the binding ratio (%) of $^{125}$I-glucagon and antiserum and the abscissa represents the initial dilution of antiserum to be tested. Numerals 1 and 2 denote Antibodies (I) and (II), respectively.

From the results shown in FIG. 5, the degree of dilution of antiserum at which the binding ratio (%) of antiserum and $^{125}$I-glucagon is 50%, i.e., activity (ID$_{50}$) of antibody was as follows:

| Antibody | Activity (ID$_{50}$) |
|---|---|
| I | about 50,000 |
| II | about 25,000 |

Pancreatic Glucagon Specificity Determination

This determination was carried out based on the principle that the proportion of labeled glucagon bound to a glucagon antibody to unlabeled glucagon bound to the glucagon antibody is identical to the proportion of concentration of labeled glucagon to that of unlabeled glucagon in the solution and that when the concentration of labeled glucagon is fixed, the amount of bound labeled glucagon (B) decreases while the amount of free labeled glucagon (F) increases as the concentration of unlabeled glucagon (glucagon to be measured) increases. Pancreatic glucagon (Standard glucagon, Concentration: 10 pg/ml to 100 ng/ml), canine gut-GLI (Dilution: 1/9 to 1/2187) and porcine gut-GLI (Dilution: 1/9 to 1/2187), were used as test samples and $^{125}$I-glucagon (10,000 cpm) was used as labeled glucagon.

200 µl of the above glucagon sample, 200 µl of $^{125}$I-glucagon and 200 µl of Antibody (I) obtained according to Example 3 (activity: about 50,000) and 100 µl of Trasylol (produced by Bayer AG, 1,000 KIU) were mixed with each other and incubated at 4° C. for 48 to 72 hours. The mixture thus treated was separated into bound labelled glucagon (B) and free labeled glucagon (F) using Dextran-coated charcoal [see M. Boyns, L. Vanhaelst and J. Goldstein; Horm. Metab. Res., 3, 409 (1971)] followed by measuring the radioactivity thereof. The binding ratio (Bo) corresponding to the activity of Antibody (I) used was defined as 100% and the percentage of bound labeled glucagon (B) of the samples at each concentration and degree of dilution was based thereon.

Figure 6:
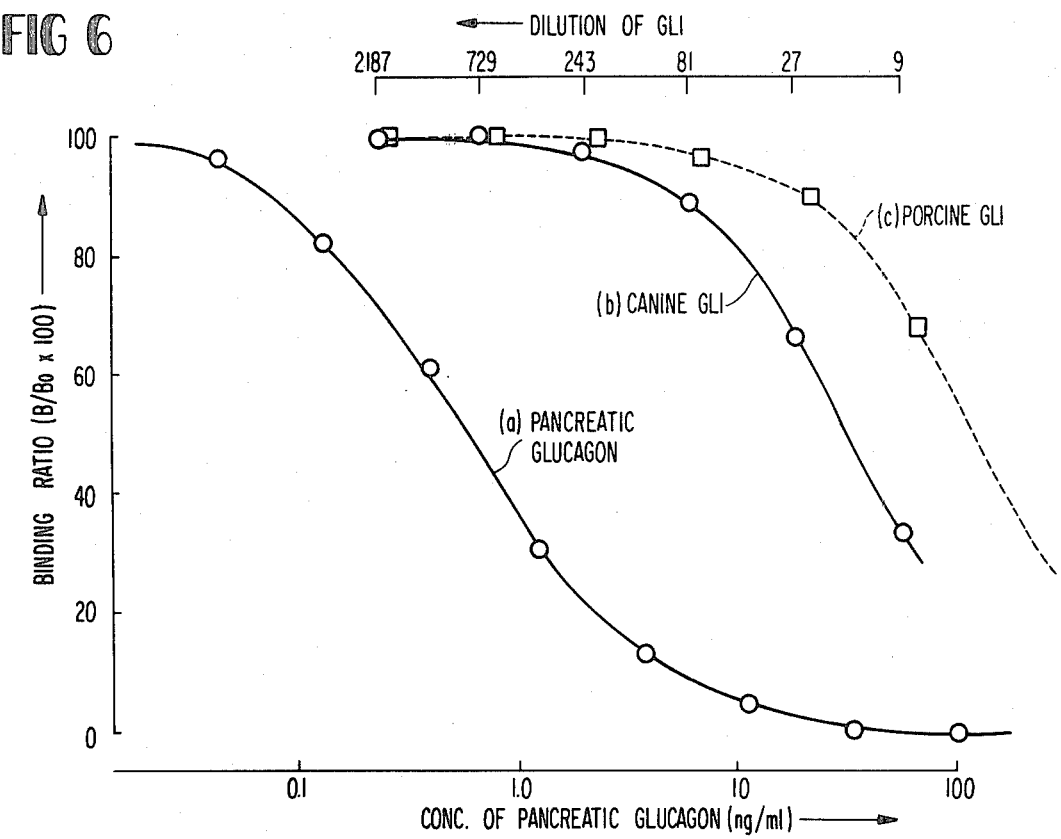
FIG. 6 shows a graph representing the specificity of the antibodies of this invention.

The results obtained are shown in FIG. 6. In FIG. 6, the ordinate represents the binding ratio (%) (B/Bo×100) and the abscissa represents the concentration of pancreatic glucagon (ng/ml) and degree of dilution of GLI. In FIG. 6, letter (a) denotes pancreatic glucagon and letters (b) and (c) denote canine gut-GLI and porcine gut-GLI, respectively.

From the results shown in FIG. 6, it can be seen that the antibody of this invention showed a curve representing reactivity with pancreatic glucagon which is clearly distinguishable from curves representing reactivity with canine and porcine gut-GLI's. From this, it follows that the antibody of this invention does not cross-react with GLI(s) and has excellent specificity to pancreatic glucagon.

In contrast, if an antibody which has low specificity to pancreatic glucagon is used, the curves representing the reactivity with canine and porcine gut-GLI's overlap the curve representing the reactivity with pancreatic glucagon and the reactivity with these GLI's is included in the reactivity with pancreatic glucagon leading to an incorrect estimation of the level of pancreatic glucagon.

EXAMPLE 4

This evaluation was carried out based on the principle of the RIA method in which labeled glucagon and unlabeled glucagon are competitively reacted with a predetermined amount of glucagon antibody in the antigen-antibody reaction.

Standard pancreatic glucagon (bovine or porcine pancreatic glucagon; concentration: 10 pg to 100 ng/ml) and canine and porcine gut-GLI(s) (dilution: 1/9 to 1/2187) were used as test samples. A mixture of 200 μl of each test sample, 200 μl of $^{125}$I-glucagon solution (containing 15 pg of $^{125}$I-glucagon; 10,000 cpm) and 200 μl of each test antibody (Antibody (I) obtained according to Example 1, 30 K and GA-10), and 100 μl of Trasylol (1,000 KIU) was incubated at 4° C. for 48 to 72 hours and the resulting bound labeled glucagon and free labeled glucagon were separated using Dextran-coated charcoal followed by measuring the radioactivity thereof in counts.

The proportion (B/T) of bound labeled glucagon (B) to total labeled glucagon (T) when no standard glucagon was added to the system was defined as 100%, and the binding ratio (%) at each concentration was measured.

Figure 7:
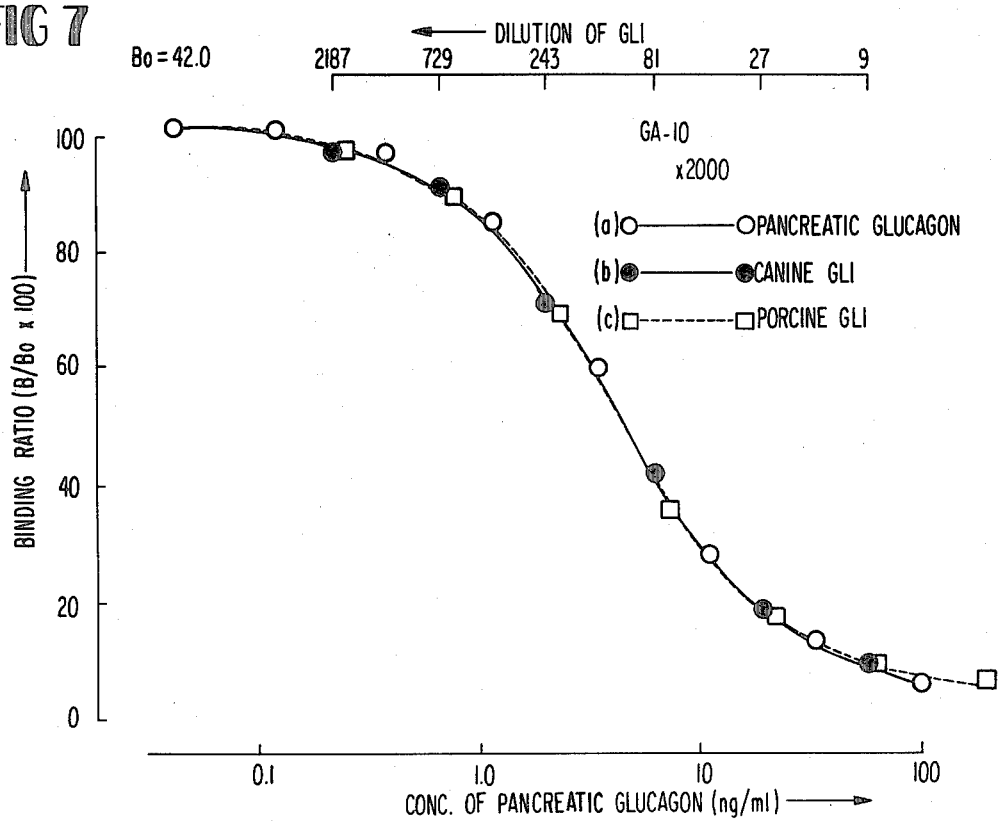
FIG. 7 is a graph showing the binding ratio (in %) of GA-10 with standard glucagon, canine gut-GLI and porcine gut-GLI at each concentration and dilution.

The results obtained are shown in FIGS. 7 to 9. In FIGS. 7 to 9 the ordinate represents the binding ratio (B/Bo×100) and the abscissa represents the concentration of pancreatic glucagon (ng/ml) and degree of dilution of gut-GLI(s). Letters (a), (b) and (c) denote standard pancreatic glucagon, canine gut-GLI and porcine gut-GLI, respectively. The interrelationship between the concentration of pancreatic glucagon and the degree of dilution was fixed as in FIG. 6. That is, using antibody Ga-10 prepared in the same manner as described in Example 1 except that syrupy glucagon fibrils were used in place of GCTR-1, the concentration of pancreatic glucagon and the degree of dilution of GLI were determined so that both of the dilution curves overlapped each other.

The interrelationship between the concentration of pancreatic glucagon and the degree of dilution of GLI thus obtained is also shown in FIGS. 8 and 9.

From the results shown in FIG. 8, it can be seen that Antibody (I) showed an immunoreactivity with pancreatic glucagon which is clearly distinguishable from the reactivity with gut-GLI. It follows from this that Antibody (I) of this invention has low cross-reactivity and is highly specific to pancreatic glucagon. From the results shown in FIG. 9, it can be seen that 30 K showed a reactivity with pancreatic glucagon which is clearly distinguished from the reactivity with gut-GLI. Therefore, 30 K has low cross-reactivity with gut-GLI and is highly specific to pancreatic glucagon.

On the other hand, when a non-specific antibody is used the reactivity with pancreatic glucagon approximates the reactivity with gut-GLI so that the curve representing pancreatic glucagon and the curve representing gut-GLI overlap each other.

It is apparent from the results shown in FIGS. 8 and 9 that Antibody (I) of this invention and known antibody 30 K showed approximately the same level of specificity to pancreatic glucagon.

EXAMPLE 5

The cross-reactivity of various peptide hormones shown in Table 1 was compared with that of standard pancreatic glucagon using Antibody (I) according to the procedure as described in Example 4.

The results obtained are shown in Table 1. In Table 1 below the cross-reactivity of the standard pancreatic glucagon measured was defined as 100% and the ratio of the observed value of other peptide hormones to that of the standard pancreatic glucagon was obtained.

Table 1

| Cross-Reactivity of Antisera Specific to Pancreatic Glucagon Against Other Peptide Hormones | |
|---|---|
| Sample | Cross-Reactivity (%) |
| Standard Pancreatic Glucagon | 100 |
| Canine Gut-GLI | 0.64 |
| Porcine Insulin** | <0.01 |
| Porcine Secretin* | <0.01 |
| Porcine CCK-PZ** | <0.01 |
| Human Gastrin* | <0.01 |
| Porcine VIP* | <0.01 |
| Porcine Motilin* | <0.01 |
| Porcine Somatostatin* | <0.01 |
| Porcine LH-RH* | <0.01 |
| Porcine Substance-P* | <0.01 |
| Porcine Neurotension* | <0.01 |

Note:
*Synthetic peptides
**Extracts
CCK-PZ = cholecystokinin-pancreozymin
VIP = vasoactive intestinal peptide
LH-RH = luteinizing hormone-releasing hormone From the results shown in Table 1 above, Antibody (I) of this invention showed a very low cross-reactivity with other peptide hormones, e.g., insulin, somatostatin, gastrin, secretin, CCK-PZ, VIP, LH-RH, motilin, etc. Although pancreatic glucagon belongs to the secretin family from a structural viewpoint, the antibody of this invention has substantially no cross-reactivity with secretin, VIP, etc. therefore, the antibody of this invention has substantially no reactivity with other similar peptide hormones.

EXAMPLE 6

30 male rabbits weighing 2.5 to 4 kg were immunized with GCTR-1 in the same manner as described in Example 3 to obtain Antibodies (III) to (XXVI). The specificity of these antibodies to pancreatic glucagon was determined in the same manner as described in Example 3 except that canine gut-GLI was used as a test sample.

The results obtained are shown in Table 2 below. In Table 2, the pancreatic glucagon equivalent obtained by measuring canine gut-GLI with GA-10 was defined as 100% and the value obtained by measuring canine gut-GLI with each antibody and the percentage of this value are shown in Table 2.

Table 2

| Difference in IRG* Values of Pooled Canine Gut Extract Measured with Each Anti-Glucagon Rabbit Serum | | |
|---|---|---|
| Antiserum | Canine Gut GLI (ng/ml PG eg.) | $\frac{\text{Each Antiserum}}{\text{GA-10}} \times 100$ (%) |
| GA-10 | 44.0 | 100.0 |
| 30-K | 0.29 | 0.64 |
| Antibody | | |
| III | 0.36 | 0.82 |
| IV | 0.48 | 1.09 |

Table 2-continued

Difference in IRG* Values of Pooled Canine Gut Extract Measured with Each Anti-Glucagon Rabbit Serum

| Antiserum | Canine Gut GLI (ng/ml PG eg.) | $\dfrac{\text{Each Antiserum}}{\text{GA-10}} \times 100$ (%) |
|---|---|---|
| V | 0.66 | 1.50 |
| VI | 0.29 | 0.64 |
| VII | 0.26 | 0.59 |
| VIII | 0.37 | 0.84 |
| IX | 0.25 | 0.57 |
| X | 0.32 | 0.72 |
| XI | 0.21 | 0.48 |
| XII | 0.61 | 1.39 |
| XIII | 0.43 | 0.98 |
| XIV | 0.27 | 0.61 |
| XV | 0.53 | 1.2 |
| XVI | 0.36 | 0.82 |
| XVII | 0.11 | 0.25 |
| XVIII | 0.13 | 0.30 |
| XIX | 0.39 | 0.89 |
| XX | 0.46 | 1.05 |
| XXI | 0.33 | 0.75 |
| XXII | 0.23 | 0.52 |
| XXIII | 0.14 | 0.32 |
| XXIV | 0.17 | 0.39 |
| XXV | 0.28 | 0.64 |
| XXVI | 0.62 | 1.41 |

*IRG: immunoreactive glucagon

From the results shown in Table 2 above, it can be seen that Antibodies (III) to (XXVI) of this invention all exhibited a specificity to pancreatic glucagon substantially the same as or better than that of 30 K. It follows from this that according to the process of this invention antibodies having specificity to pancreatic glucagon not lower than 30 K which has been considered to be the best known with respect to specificity to pancreatic glucagon were obtained with quite good reproducibility.

While the invention has been described in detail and with reference to specific embodiments thereof, it will be apparent to one skilled in the art that various changes and modifications can be made therein without departing from the spirit and scope thereof.

What is claimed is:

1. A method for preparing a pancreatic glucagon specific antibody which comprises administering as an antigen a peptide-protein complex of a peptide represented by the formula (I):

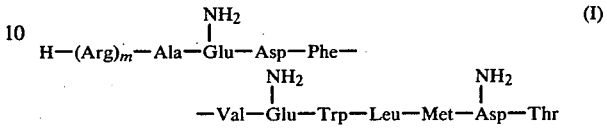

wherein m is 0 or 1, linked to a protein carrier which is equine serum albumin, bovine serum albumin, rabbit serum albumin, human serum albumin, equine serum globulin, bovine serum globulin, rabbit serum globulin or human serum globulin by a dialdehyde represented by the general formula (II):

$$OHC-(CH_2)_n-CHO \qquad (II)$$

wherein n is an integer of 1 to 5 to a mammal to produce an antibody and recovering the resulting pancreatic glucagon specific antibody.

2. The method of claim 1, wherein m is 0.

3. The method of claim 1, wherein m is 1.

4. The method of claim 1, wherein said dialdehyde is malonaldehyde, succinaldehyde, glutaraldehyde, or adipaldehyde.

5. The method of claim 1, wherein the antigen contains 9 to 12 moles of peptide per mole of protein.

6. The method of claim 1, wherein said antigen is administered in an amount of about 0.5 to about 2 mg of said antigen per administration and said administering is repeated every two weeks for about 2 to 10 months.

7. A pancreatic glucagon specific antibody produced according to the method of claim 1.

* * * * *